United States Patent [19]

Smith, III et al.

[11] Patent Number: 5,206,233
[45] Date of Patent: Apr. 27, 1993

[54] SUBSTITUTED THIAZEPINES AS CENTRAL NERVOUS SYSTEM AGENTS

[75] Inventors: William J. Smith, III; Lawrence D. Wise; David J. Wustrow, all of Ann Arbor, Mich.

[73] Assignee: Warner-Lambert Company, Morris Plains, N.J.

[21] Appl. No.: 750,667

[22] Filed: Aug. 27, 1991

[51] Int. Cl.$^5$ .................... C07D 28/106; A61K 31/55
[52] U.S. Cl. ........................................ 514/211; 540/544
[58] Field of Search ........................ 514/211; 540/544

[56] References Cited

PUBLICATIONS

Largent, et al. J. of Pharmacol. and Exp. Therapeutics, vol. 238(2) 1986 pp. 739–748.
Tam, Proc. Natl. Acad. Sci, USA 80 pp. 6703–6707, 1983.
The Merck Manual, (Rahway, N.J. Merck and Co., 1992) pp. 1614–1644.
The Merck Manual (Rahway, N.J. Merck and Co., 1981) pp. 1518–1522 and 1540–1541.
Guy et al., Drug Devol. Res. 3:245–252 (1983).
Lindstrom et al., Psychopharm. (1985) 86:241–243.
Chouinard et al., Psychopharm. (1984) 84:282–284.
Chouinard et al., Psychopharm. Bull. 22(1) 1985-pp. 267–271.
Rao, et al, Neuropharm. 29(12) pp. 1191–1197, 1990.
McLean, et al., Pharm. Biochem. and Behavior 8 97–99, 1978.
Bass, et al., J. Pharmacol. Exp. Therapeutics 186(1) 1973 pp. 183–198.
Walker, et al., Pharmacol. Rev. 1990, 42(4) pp. 355–402.
Kumar, Jain et al., Int. Clin. Psychopharm 1987(2) 129–133.
Rao et al., Neuropharm. 29(12) 1199–1204, 1990.
Pontecorvo et al., Brain Res. Bull., 26 pp. 461–465, 1991.
Lobner et al., Neuroscience Letters 117 (1990) 169–174.
Campbell et al., J. of Neuroscience 1989 9(10) 3380–3391.
Moore et al, Amer. Coll. Neuropsychopharm. Abstract, p. 149, (1985).

*Primary Examiner*—Robert T. Bond
*Assistant Examiner*—E. C. Ward
*Attorney, Agent, or Firm*—Francis J. Tinney

[57] ABSTRACT

Substituted thiazepines are described as well as methods for the preparation and pharmaceutical composition of same, which are useful as central nervous system agents and are particularly useful as antipsychotic and antidepressant agents as well as for treating cerebral ischemia or cerebral infarction.

6 Claims, No Drawings

SUBSTITUTED THIAZEPINES AS CENTRAL NERVOUS SYSTEM AGENTS

BACKGROUND OF THE INVENTION

The present invention relates to novel substituted thiazepines useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention bind to the sigma receptor.

A number of benzomorphan opioids which selectively bind to the sigma receptor induce psychotic-like states in humans (Largent, B. L., et al, *Journal of Pharmacology and Experimental Therapeutics*, 238:739–748 (1986) and Tam, S. W., *Proceedings of the National Academy of Sciences, USA* 80:6703–6707 (1983)). Additionally, it has been reported that many known antipsychotic agents interact with the sigma receptor (Walker, M. J., et al, *Pharmacological Reviews* 42:355–402 (1990)). These include haloperidol, rimcazole, remoxapride, and tiospirone (Jain, A. K., et al, *International Clinical Psychopharmacology* 2:129–133 (1987); Guy, W., et al, *Drug Development Research*, 3:245–252 (1983); Moore, N. C., et al, *American College of Neuropsychopharmacology, Abstract*, p. 149 (1985); Lindstrom, L., et al, *Psychopharmacology* 86:241–243 (1985); Chouinard, G. and Annable, L., *Psychopharmacology* 84:282–284 (1984); and Chouinard, G. and Turner, L., *Psychopharmacology Bulletin* 22:267–271 (1986)).

We have surprisingly and unexpectedly found that a series of substituted thiazepines potently and selectively bind to the sigma receptor and are thus useful in the treatment of various psychotic disorders and in particular schizophrenia.

SUMMARY OF THE INVENTION

Accordingly, the present invention is a compound of Formula I

I wherein R is hydrogen, lower alkyl, lower alkoxy, hydroxy, halogen, amino, nitro, trifluoromethyl, or cyano; and
$R^1$ is wherein $R^2$ is hydrogen, lower alkyl, —(CH$_2$)$_n$—$R^3$
wherein $R^3$ is and n is an integer of 1, 2, 3, 4, or 5;

$$-(CH_2)_{n-1}-\overset{O}{\underset{\|}{C}}-R_3$$

wherein $R^3$ and n are as defined above or $$-C\underset{\diagdown}{\diagup}(CH_2)_m$$

wherein m is an integer of 2, 3, 4, 5, or 6; and corresponding optical isomers thereof; or a pharmaceutically acceptable acid addition salt thereof.

As sigma ligands, the compounds of Formula I are useful as antipsychotic agents for treating psychoses such as schizophrenia. They are also useful as antidepressants (see Rao, T.S., et al, *Neuropharmacology* 29(12):1191–1197 (1990) and Rao, T. S., et al, *Neuropharmacology* 29(12):1199–1204 (1990)) and as cerebroprotective agents useful in treating cerebral ischemia and cerebral infarction (see Pontecorvo, M. J., et al, *Brain Research Bulletin* 26:461–465 (1991) and Lobner, D. and Lipton, P., *Neuroscience Letters* 117:169–174 (1990)).

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n propyl, isopropyl, n-butyl, sec-butyl, isobutyl, tert-butyl, n-pentyl, n-hexyl, and the like.

"Lower alkoxy" is O-alkyl of from one to six carbon atoms as defined above for "lower alkyl".

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, bisulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science* 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvate forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is hydrogen, lower alkoxy, or halogen;

$R^2$ is hydrogen, lower alkyl, —(CH$_2$)$_n$—R$^3$

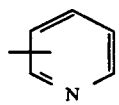

and n is an integer of 3, 4, or 5,

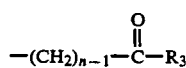

wherein R$^3$ and n are as defined above or

wherein m is an integer of 4, 5, or 6.

Another preferred embodiment is a compound of Formula I wherein R is hydrogen, 4-methoxy, or 4-chloro;

$R^2$ is hydrogen, lower alkyl, —(CH$_2$)$_4$—R$^3$ wherein R$^3$ is

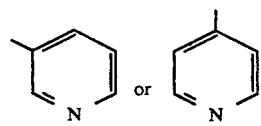

wherein R$^3$ is as defined above or

Particularly valuable are:
Hexahydro-7-(4-methoxyphenyl)-4 methyl-1,4-thiazepine, hydrochloride;
Hexahydro-7-(4-methoxyphenyl)-4-ethyl-1,4-thiazepine;
Hexahydro-7-(4 methoxyphenyl)-4 isopropyl-1,4-thiazepine, hydrochloride;
Hexahydro-7-(4-methoxyphenyl)-4-cyclopentyl-1,4-thiazepine, hydrochloride;
Hexahydro-7-(4-chlorophenyl)-4-methyl-1,4-thiazepine, hydrochloride;
Hexahydro 7-phenyl-4-methyl 1,4-thiazepine;
Hexahydro-7-phenyl-4-isopropyl-1,4-thiazepine;
Hexahydro-7-(4-methoxyphenyl)-4-propyl-1,4-thiazepine;
Hexahydro-7-(4-chlorophenyl) 4-propyl-1,4-thiazepine;
Hexahydro-7-(4-chlorophenyl)-4-ethyl-1,4-thiazepine;
Hexahydro-7-(4-methoxyphenyl) 4-[4-(4-pyridinyl)butyl]-1,4-thiazepine;
1-(3-Pyridinyl)-7-(4-methoxyphenyl)-4-(tetrahydro-1,4-thiazepin-4(2H)-yl)-1-butanone, dihydrochloride;
Hexahydro-7-(phenyl)-4-[4-(4-pyridinyl) butyl]-1,4-thiazepine, hydrochloride;
Hexahydro-7-(phenyl)-4-[4-(3-pyridinyl)butyl]1,4 thiazepine;
Hexahydro-7 (4-chlorophenyl)-4-[4-(4-pyridinyl)butyl]-1,4-thiazepine;
2,3,4,5-Tetrahydro-7-phenyl-4-[4-(4-pyridinyl)butyl]-1,4-thiazepine;
Hexahydro-7 (4-methoxyphenyl)-1,4-thiazepine; and
7-Phenyl-2,3,4,5-tetrahydro-1,4-thiazepine; and corresponding optical isomers thereof; or a pharmaceutically acceptable acid addition salt thereof.

The compounds of Formula I are valuable sigma ligands. The tests employed indicate that compounds of Formula I possess sigma binding activity and are thus useful in treating psychoses such as schizophrenia, as well as conditions such as depression, cerebral ischemia, and cerebral infarction. The data in the table show the inhibition of 3-PPP((+)-[$^3$H]-3[3-hydroxyphenyl]-N-(1-propyl)piperidine; a sigma ligand) binding by representative compounds of Formula I, according to the method of Largent, B. L., et al, *Journal of Pharmacology and Experimental Therapeutics* 238:739–748 (1986). Additionally, the compounds of Formula I were tested for their ability to inhibit locomotor activity in mice according to the assay described by McLean, J. R., et al, *Pharmacology, Biochemistry and Behavior* 8:97–99 (1978); for their ability to inhibit contractions of electrically stimulated guinea pig ileum according to the method of Campbell, B. G., et al, *Journal of Neurosci-* ence 9 3380-3384 (1989) and Bass, P., et al, *Journal of Pharmacology and Experimental Therapeutics* 186:183-198 (1973). These tests further support the antipsychotic activity of the compounds of Formula I.

The above test methods are incorporated herein by reference. The data in the table show the activity of representative compounds of Formula I.

| | Biological Activity of Compounds of Formula I | | | |
|---|---|---|---|---|
| Example Number | Compound | Inhibition of Locomotor Activity in Mice ED$_{50}$, mg/kg, IP | Inhibition of Contraction of Electrical Stimulation Guinea Pig Ileum IC$_{50}$, μM | 3-PPP Binding IC$_{50}$, mM |
| 2 | Hexahydro-7-(4-methoxyphenyl)-4-methyl-1,4-thiazepine, hydrochloride | | | 16.5 |
| 3 | Hexahydro-7-(4-methoxyphenyl)-4-ethyl-1,4-thiazepine | | | 6.22 |
| 4 | Hexahydro-7-(4-methoxyphenyl)-4-isopropyl-1,4-thiazepine, hydrochloride | | | 1.62 |
| 6 | Hexahydro-7-(4-chlorophenyl)-4-methyl-1,4-thiazepine, hydrochloride | | | 121 |
| 10 | Hexahydro-7-(4-chlorophenyl)-4-propyl-1,4-thiazepine | | | 21.31 |
| 12 | Hexahydro-7-(4-methoxyphenyl)-4-[4-(4-pyridinyl)butyl]-1,4-thiazepine | 13.9 | 7.3 | 1.32 |
| 13 | 1-(3-Pyridinyl)-7-(4-methoxyphenyl)-4-(tetrahydro-1,4-thiazepin-4(2H)-yl)-1-butanone, dihydrochloride | | | 9.2 |
| 14 | Hexahydro-7-(phenyl)-4-[4-(4-pyridinyl)butyl]-1,4-thiazepine, hydrochloride | 13.1 | 13.1 | 6.39 |
| 15 | Hexahydro-7-(phenyl)-4-[4-(3-pyridinyl)butyl]-1,4-thiazepine | 17.9 | 4.00 | 2.5 |
| 16 | Hexahydro-7-(4-chlorophenyl)-4-[4-(4-pyridinyl)butyl]-1,4-thiazepine | 19.0 | | 2.62 |

A compound of Formula Ia

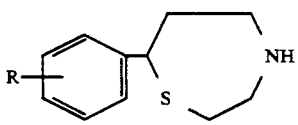

Ia wherein R is hydrogen, lower alkyl, lower alkoxy, hydroxy, halogen, amino, nitro, trifluoromethyl, or cyano; and corresponding optical isomers thereof; or a pharmaceutically acceptable acid addition salt thereof, may be prepared by reacting a compound of Formula II

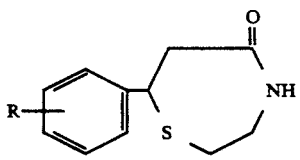

II wherein R is as defined above with a hydride reagent such as, for example, aluminum hydride and the like in a solvent such as, for example, diethyl ether, tetrahydrofuran, and the like at about 0° C. to about 25° C. for about 30 minutes to about 24 hours to afford a compound of Formula Ia. Preferably, the reaction is carried out with aluminum hydride in diethyl ether-tetrahydrofuran at about 25° C. for about 12 hours.

A compound of Formula Ib

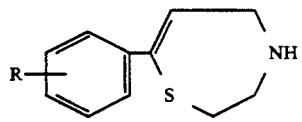

Ib wherein R is hydrogen, lower alkyl, lower alkoxy, hydroxy, halogen, amino, nitro, trifluoromethyl, or cyano; and corresponding optical isomers thereof; or a pharmaceutically acceptable acid addition salt thereof may be prepared by reacting a compound of Formula III

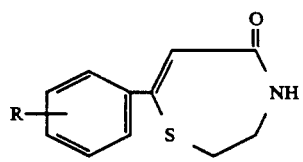

III wherein R is as defined above with a hydride reagent such as, for example, lithium aluminum hydride and the like in a solvent such as, for example, diethyl ether and the like at about 0° C. to about 25° C. for about 30 minutes to about 24 hours to afford a compound of Formula Ib. Preferably, the reaction is carried out with lithium aluminum hydride in diethyl ether at about 25° C. for about 12 hours.

A compound of Formula Ic

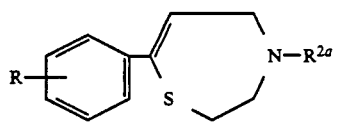
Ic wherein R is hydrogen, lower alkyl, lower alkoxy, hydroxy, halogen, amino, nitro, trifluoromethyl, or cyano and $R^{2a}$ is lower alkyl or

wherein m is an integer of 2, 3, 4, 5, or 6; and corresponding optical isomers thereof; or a pharmaceutically acceptable acid addition salt thereof may be prepared by reacting a compound of Formula Ia

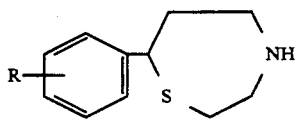
Ia wherein R is as defined above with a compound of Formula IV

IV wherein $R^{2a}$ is as defined above in the presence of sodium cyanoborohydride and the like and an acid such as, for example, acetic acid at about 25° C. for about 30 minutes to about 12 hours to afford a compound of Formula Ic. Preferably, the reaction is carried out with sodium cyanoborohydride and acetic acid at about 25° C. for about 2 hours.

A compound of Formula Id

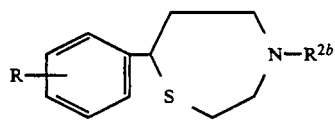
Id wherein R is hydrogen, lower alkyl, lower alkoxy, hydroxy, halogen, amino, nitro, trifluoromethyl, or cyano, and $R^{2b}$ is lower alkyl; and corresponding optical isomers thereof; or a pharmaceutically acceptable acid addition salt thereof may be prepared by reacting a compound of Formula V

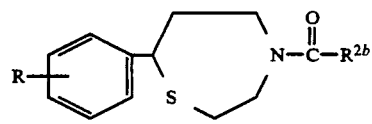
V wherein R and $R^{2b}$ are as defined above with a hydride reagent such as, for example, aluminum hydride and the like in a solvent such as, for example, diethyl ether, tetrahydrofuran and the like at about 0° C. to about 25° C. for 30 minutes to about 12 hours to afford a compound of Formula Id. Preferably, the reaction is carried out with aluminum hydride in diethyl ether-tetrahydrofuran at about 25° C. for about 8 hours.

A compound of Formula Ie

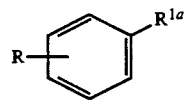
Ie wherein R is hydrogen, lower alkyl, lower alkoxy, hydroxy, halogen, amino, nitro, trifluoromethyl, or cyano; and
$R^{1a}$ is

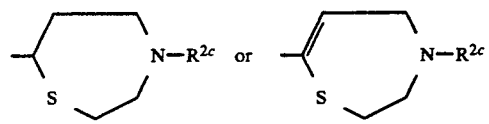

wherein $R^{2c}$ is lower alkyl —$(CH_2)_n$—$R^3$ wherein $R^3$ is

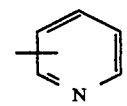

and n is an integer of 1, 2, 3, 4, or 5, or

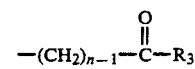

wherein $R^3$ and n are as defined above; and corresponding optical isomers thereof; or a pharmaceutically acceptable acid addition salt thereof may be pepared by reacting either a compound of Formula Ia or Formula Ib

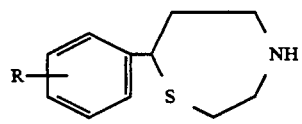
Ia

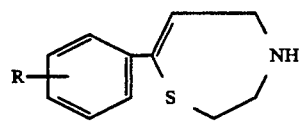
Ib with a compound of Formula VI

VI wherein Hal is halogen and $R^{2c}$ is as defined above in the presence of a base such as, for example, an alkali metal or alkaline earth metal carbonate or bicarbonate, for example, potassium bicarbonate and the like in a solvent such as, for example, acetonitrile and the like at about 25° C. to about the reflux temperature of the solvent for about 1 hour to about 24 hours to afford a compound of Formula Ie. Preferably, the reaction is carried out with potassium bicarbonate in acetonitrile at about reflux for about 24 hours.

A compound of Formula II wherein R is as defined above may be prepared by reacting a compound of Formula VII

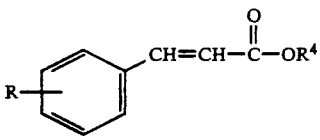
VII wherein $R^4$ is lower alkyl and R is as defined above with 2 aminoethanethiol hydrochloride in the presence of a base such as, for example, an alkali metal or alkaline earth metal hydroxide or carbonate and the like, for example, sodium hydroxide in a solvent such as, for example, methanol and the like at about 0° C. to about 60° C. for about 1 hour to about 5 days to afford a compound of Formula II. Preferably, the reaction is carried out with sodium hydroxide in methanol at about 60° C. for about 5 days.

A compound of Formula III wherein R is as defined above may be prepared by reacting a compound of Formula II wherein R is as defined above with sulfuryl chloride in a solvent such as, for example, dichloromethane and the like at about −5° C. to about 25° C. for about 1 hour to about 8 hours to afford a compound of Formula III. Preferably, the reaction is carried out in dichloromethane at about −5° C. to about 25° C. for about 8 hours.

A compound of Formula V wherein R and $R^{2b}$ are as defined above may be prepared by reacting a compound of Formula Ia with a compound of Formula VIII

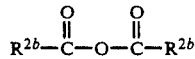
VIII wherein $R^{2b}$ is as defined above in the presence of a base such as, for example, triethylamine and the like in a solvent such as, for example, tetrahydrofuran and the like to afford a compound of Formula V. Preferably, the reaction is carried out in tetrahydrofuran.

Compounds of Formula IV, Formula VI, Formula VII, and Formula VIII are either known or capable of being prepared by methods known in the art.

Additionally, wherein a compound of Formula I is a racemic mixture, it may be further resolved into its enantiomers. Accordingly, as another aspect of the present invention, a compound of Formula (±) I may be resolved into its enantiomers by the use of conventional methodology such as, for example, optically active acids. Thus, the resulting diastereomeric salts may be separated by crystallization and then converted by conventional methodology to the optically active enantiomer (+)I or (−) I.

The compounds of the present invention can be prepared and administered in a wide variety of oral and parenteral dosage forms. It will be obvious to those skilled in the art that the following dosage form may comprise as the active component either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gum, resins, methylcellulose, sodium carboxymethylcellulose, and other well-known suspending agents.

Also included are solid form preparations which are intended to be converted, shortly before use, to liquid form preparations for oral administration. Such liquid form include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

Hexahydro-7-(4-methoxyphenyl)-1,4-thiazepine, hydrochloride

Step (a): Preparation of Tetrahydro-7-(4-methoxyphenyl)-1,4-thiazepin-5-one

A mixture of 2-aminoethanethiol hydrochloride (31.0 g, 0.273 mol) and 140 mL of methanol is cooled to 0° C. and treated with pulverized sodium hydroxide (12.0 g, 0.475 mol) followed by trans-methyl 4-methoxycinnamate (52.4 g, 0.273 mol). The reaction mixture is allowed to warm to room temperature and stirred for 5 days. The mixture is then heated to 60° C. for 30 minutes and filtered while still warm. The methanolic solution is concentrated to ca ¼ volume and the product is isolated by filtration (35 g).

Step (b): Preparation of Hexahydro-7-(4-methoxyphenyl)-1,4-thiazepine

Lithium aluminum hydride (190 mL of a 1M ethereal solution) is cooled to 0° C. and treated with aluminum chloride (8.44 g, 63.2 mmol) in 15 mL of diethyl ether. The resulting clear solution is stirred at 0° C. for 20 minutes and then a slurry of tetrahydro-7-(4-methoxyphenyl)-1,4-thiazepin 5-one (15.0 g, 63.2 mmol) in 150 mL of tetrahydrofuran is added. The reaction is then allowed to warm to room temperature for 12 hours and is treated with 14.4 mL of water, 7.2 mL of a 10% aqueous sodium hydroxide solution and 36 mL of water. The mixture is stirred for 3 hours and filtered. The filtrate is concentrated to obtain 8.14 g of a clear oil. The oil is converted to the hydrochloride salt; mp 209°-212° C.

EXAMPLE 2

Hexahydro-7-(4-methoxyphenyl)-4-methyl-1,4-thiazepine, hydrochloride

To 30 mL of acetonitrile is added hexahydro-7 (4-methoxyphenyl)-1,4-thiazepine (Example 1) (1.00 g, 4.48 mmol), an aqueous formaldehyde solution (5 mL, 57 mmol), sodium cyanoborohydride (0.30 g, 4.48 mmol) and 1 mL of acetic acid. The reaction is stirred for 2 hours and is then diluted with 40 mL of water, made basic with 15% aqueous sodium hydroxide solution and extracted with four 150 mL portions of chloroform. The combined organic layers are dried and concentrated to obtain 0.75 g of a clear oil. The oil is converted to the hydrochloride salt; mp 177° C.

In a process analogous to Example 2 using appropriate starting materials the corresponding compounds of Formula I are prepared as follows:

EXAMPLE 3

Hexahydro-7-(4-methoxyphenyl)-4-ethyl 1,4-thiazepine m/z 251.

EXAMPLE 4

Hexahydro-7-(4-methoxyphenyl)-4-isopropyl-1,4-thiazepine, hydrochloride mp 162°-163° C.

EXAMPLE 5

Hexahydro-7-(4 methoxyphenyl)-4-cyclopentyl-1,4-thiazepine, hydrochloride mp 196°-198° C. (dec).

EXAMPLE 6

Hexahydro-7-(4-chlorophenyl)-4-methyl-1,4-thiazepine hydrochloride

147°-149° C. (dec).

EXAMPLE 7

Hexahydro-7-phenyl-4-methyl 1,4-thiazepine m/z 207.

EXAMPLE 8

Hexahydro-7-phenyl-4-isopropyl-1,4-thiazepine m/z 235.

EXAMPLE 9

Hexahydro-7-(4-methoxyphenyl)-4-propyl-1,4-thiazepine

Step (a): Preparation of Hexahydro-4-propionyl-7-(4-methoxyphenyl) 1,4-thiazepine Hexahydro-7-(4-methoxyphenyl)-1,4-thiazepine (Example 1) (1.5 g, 6.72 mmol) is added to 25 mL of tetrahydrofuran. The reaction mixture is stirred while propionic anhydride (1.32 g, 10.1 mmol) and triethylamine (1.02 g, 10.1 mmol) are added. The reaction mixture is concentrated under reduced pressure and is partitioned between 1N hydrochloric acid and chloroform. The organic layer is washed with a saturated aqueous solution of sodium bicarbonate, dried with sodium sulfate, and concentrated. The reaction mixture is further purified by column chromatography on silica eluting with 98% chloroform, 2% methanol, and 0.1% anhydrous ammonia to obtain 1.10 g of a clear, colorless viscous oil which solidifies on standing; mp 134°-135° C.

Step (b): Preparation of Hexahydro-7-(4-methoxtphenyl)-4-propyl-1,4-thiazepine

A solution of lithium aluminum hydride (24 mL of a 1 M ethereal solution) is chilled to 0° C. and treated with aluminum chloride (1.08 g, 8.00 mmol) in ca 5 mL of anhydrous diethyl ether. The clear reaction mixture is stirred for ca 20 minutes at 0° C. before a solution of hexahydro-4-propionyl-7-(4-methoxyphenyl)-1,4- thiazepine (2.20 g, 7.75 mmol) is added in 10 mL of tetrahydrofuran. The reaction mixture is allowed to warm to room temperature over an 8 hour period and quenched by careful addition of 2 mL of water, followed by 1 mL of 15% aqueous sodium hydroxide solution, and finally 5 mL of water at 0° C. The reaction is stirred at room temperature for ca 2 hours, filtered, and the filtrate is concentrated and purified by column chromatography on silica eluting with 98% chloroform, 2% methanol, and 0.1% anhydrous ammonia, to yield 1.30 g of an oil which is converted to its hydrochloride salt; mp 117°–119° C.

In a process analogous to Example 9 using appropriate starting materials the corresponding compounds of Formula I are prepared as follows:

EXAMPLE 10

Hexahydro-7-(4-chlorophenyl)-4-propyl-1,4-thiazepine m/z 269.

EXAMPLE 11

Hexahydro 7-(4-chlorophenyl)-4-ethyl

-1,4-thiazepine m/z 255.

EXAMPLE 12

Hexahydro-7-(4-methoxyphenyl)-4-[4-(4 pyridinyl)-butyl]-1,4-thiazepine

To 25 mL of acetonitrile is added 1-(4-pyridinyl)-4-chlorobutane (2.00 g, 11.8 mmol), hexahydro-7-(4 methoxyphenyl)-1,4-thiazepine (Example 1) (2.63 g, 11.8 mmol), and anhydrous potassium bicarbonate (2.65 g, 47.2 mmol). The reaction mixture is heated to reflux under an atmosphere of nitrogen for 24 hours. The reaction mixture is then filtered, the filtrate concentrated, and the resulting residue is purified by column chromatography on silica eluting with 98% chloroform, 2% methanol, and 0.1% anhydrous ammonia to yield 1.58 g of the desired product; m/z 356.

In a process analogous to Example 12 using appropriate starting materials the corresponding compounds of Formula I are prepared as follows:

EXAMPLE 13

1-(3-Pyridinyl)-7-(4-methoxyphenyl)

-4 (tetrahydro-1,4-thiazepin-4(2H)-yl)

-1-butanone, dihydrochloride mp 211°–212° C.

EXAMPLE 14

Hexahydro-7-(phenyl)-4-[4-(4-pyridinyl) butyl]1,4-thiazepine, hydrochloride mp 139°–140° C.

EXAMPLE 15

Hexahydro-7-(phenyl)-4-[4-(3 -pyridinyl)butyl]-1,4-thiazepine m/z 326.

EXAMPLE 16

Hexahydro-7-(4-chlorophenyl)-4-[4 -(4-pyridinyl)butyl]-1,4-thiazepine mp 139°–140° C.

EXAMPLE 17

7-Phenyl-2,3,4,5-tetrahydro-1,4

-thiazepine

Step (a): Preparation of 3,4-Dihydro-7-phenyl -1,4-thiazepine-5(2H)-one

Tetrahydro-7-phenyl-1,4-thiazepin-5(2H) one (6.23 g, 30.1 mmol) is slurried in 150 mL of dichloromethane. The reaction is cooled to −5° C. and sulfuryl chloride (31.0 mL of a 1M solution in dichloromethane) is added. The reaction mixture is stirred for 3 hours at −5° C. then allowed to warm to room temperature for 8 hours. The reaction mixture is concentrated to dryness under a stream of nitrogen and the residue is slurried in 50 mL of dichloromethane and stirred with a saturated solution of sodium bicarbonate. The organic layer is separated and the aqueous layer is extracted with dichloromethane. The combined organic layers are dried over sodium sulfate and concentrated under reduced pressure to obtain 4.13 g of a white solid; mp 148°–150° C.

Step (b): Preparation of 7-Phenyl-2,3,4,5-tetrahydro-1,4-thiazepine 3,4-Dihydro-7-phenyl-1,4-thiazepin-5(2H)-one (3.30 g, 16.2 mm cl) is added to 50 mL of absolute diethyl ether. The reaction mixture is then cooled to 0° C. and lithium aluminum hydride (16.7 mL of a 1M ethereal solution) is added. The reaction mixture is then stirred overnight at room temperature and is quenched by the addition of 2.5 mL of water followed by 5 mL of 10% aqueous sodium hydroxide solution. The solids are filtered and washed with absolute ethanol. The filtrates are combined and concentrated under reduced pressure and the resulting residue is chromatographed on silica eluting with 10:1 dichloromethane:methanol to obtain 1.63 g of the product as a clear oil.

EXAMPLE 18

2,3,4,5-Tetrahydro-7-phenyl-4-[4

-(4-pyridinyl)butyl]-1,4-thiazepine 1-(4-Pyridyl)-4 chlorobutane is reacted with the 7-phenyl-2,3,4,5-tetrahydro 1,4-thiazepine (Example 17) using the procedure of Example 12 to give the desired product after column chromatography; m/z 324.

We claim:

1. A compound of Formula I

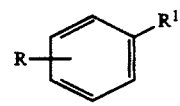

wherein
R is hydrogen, lower alkyl, lower alkoxy, hydroxy, halogen, amino, nitro, trifluoromethyl, or cyano; and
$R^1$ is

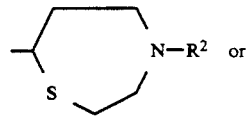

-continued

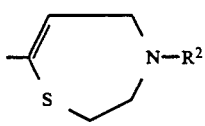

wherein R² is hydrogen, lower alkyl, —(CH₂)ₙ—R³ wherein R³ is

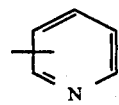

and n is an integer of 1, 2, 3, 4, or 5;

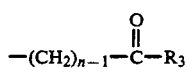

wherein R³ and n are as defined above or

wherein m is an integer of 2, 3, 4, 5, or 6; and corresponding optical isomers thereof; or a pharmaceutically acceptable acid addition salt thereof.

2. A compound according to claim 1 in which
R is hydrogen, lower alkoxy, or halogen;
R² is hydrogen, lower alkyl, —(CH₂)ₙ—R³ wherein R³ is

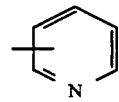

and n is an integer of 3, 4, or 5,

wherein R³ and n are as defined above or

wheein m is an integer of 4, 5, or 6.
3. A compound according to claim 2 in which
R is hydrogen, 4-methoxy, or 4-chloro;

R² is hydrogen, lower alkyl, —(CH₂)₄—R³ wherein R³ is

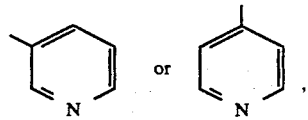

wherein R³ is as defined above or

4. A compound according to claim 3 selected from the group consisting of:
Hexahydro-7-(4-methoxyphenyl)-4-methyl-1,4-thiazepine, hydrochloride;
Hexahydro-7-(4-methoxyphenyl) -4-ethyl-1,4-thiazepine;
Hexahydro-7-(4-methoxyphenyl) -4-isopropyl-1,4-thiazepine, hydrochloride;
Hexahydro-7-(4-methoxyphenyl)-4-cyclopentyl-1,4-thiazepine, hydrochloride;
Hexahydro-7-(4-chlorophenyl)-4-methyl-1,4-thiazepine, hydrochloride;
Hexahydro-7-phenyl 4-methyl-1,4-thiazepine;
Hexahydro-7-phenyl-4-isopropyl-1,4-thiazepine;
Hexahydro-7-(4-methoxyphenyl)-4-propyl-1,4-thiazepine;
Hexahydro-7-(4-chlorophenyl)-4-propyl-1,4-thiazepine;
Hexahydro-7-(4-chlorophenyl)-4-ethyl-1,4-thiazepine;
Hexahydro-7-(4-methoxyphenyl)-4-[4-(4-pyridinyl)-butyl]-1,4-thiazepine;
1-(3-Pyridinyl)-7-(4-methoxyphenyl)-4-(tetrahydro-1,4-thiazepin-4(2H)-yl)-1-butanone, dihydrochloride;
Hexahydro-7-(phenyl)-4-[4-(4-pyridinyl)-butyl]-1,4-thiazepine, hydrochloride;
Hexahydro-7-(phenyl)-4-[4-(3-pyridinyl) -butyl]-1,4-thiazepine;
Hexahydro-7-(4-chlorophenyl)-4-[4-(4-pyridinyl)-butyl]-1,4-thiazepine;
2,3,4,5-Tetrahydro-7-phenyl-4-[4-(4-pyridinyl)butyl]-1,4-thiazepine;
Hexahydro-7-(4-methoxyphenyl)-1,4-thiazepine; and
7-Phenyl-2,3,4,5-tetrahydro-1,4-thiazepine.

5. A method of treating schizophrenia, comprising administering to a host suffering therefrom a therapeutic effective amount of a compound according to claim 1 in unit dosage form.

6. A pharmaceutical composition adapted for administration as an agent for treating schizophrenia comprising a therapeutic effective amount of a compound according to claim 1 in admixture with a pharmaceutically acceptable excipient, diluent or carrier.

* * * * *

UNITED STATES PATENT AND TRADEMARK OFFICE
CERTIFICATE OF CORRECTION

PATENT NO. : 5,206,233
DATED : April 27, 1993
INVENTOR(S) : W.J. Smith, III, et al.

It is certified that error appears in the above-indentified patent and that said Letters Patent is hereby corrected as shown below:

In Column 15, line 49, delete "$-C \quad (CH_2)_m$"

and insert -- $-(CH_2)_{n-1}-\overset{O}{\underset{}{C}}-R^3$ --

In Column 15, line 56, delete "$-C \quad (CH_2)_m$"

and insert --  --

UNITED STATES PATENT AND TRADEMARK OFFICE
CERTIFICATE OF CORRECTION

PATENT NO. : 5,206,233
DATED : April 27, 1993
INVENTOR(S) : W.J. Smith, III, et al.

It is certified that error appears in the above-indentified patent and that said Letters Patent is hereby corrected as shown below:

In column 16, line 9, insert $$-- -(CH_2)_3-\overset{\overset{O}{\|}}{C}-R^3 --$$

Signed and Sealed this

Twenty-first Day of December, 1993

*Attest:*

BRUCE LEHMAN

*Attesting Officer*     Commissioner of Patents and Trademarks